United States Patent
Milius et al.

(10) Patent No.: US 6,670,306 B2
(45) Date of Patent: Dec. 30, 2003

(54) HERBICIDE COMPOSITION COMPRISING GLYPHOSATE AND AT LEAST A POLYXYLOSIDE ALKYL

(75) Inventors: Alain Milius, Nice (FR); Bernard Brancq, Le Chesnay (FR)

(73) Assignee: Société d'Exploitation de Produits pour les Industries Chimiques SEPPIC, Paris (FR)

( * ) Notice: Subject to any disclaimer, the term of this patent is extended or adjusted under 35 U.S.C. 154(b) by 0 days.

(21) Appl. No.: 10/332,734

(22) PCT Filed: Jul. 11, 2001

(86) PCT No.: PCT/FR01/02235

§ 371 (c)(1),
(2), (4) Date: May 16, 2003

(87) PCT Pub. No.: WO02/03802

PCT Pub. Date: Jan. 17, 2002

(65) Prior Publication Data

US 2003/0176285 A1 Sep. 18, 2003

(30) Foreign Application Priority Data

Jul. 11, 2000 (FR) .............................................. 00 09035

(51) Int. Cl.⁷ ........................ A01N 25/30; A01N 57/02
(52) U.S. Cl. ....................................... 504/206; 504/358
(58) Field of Search ................................. 504/206, 358

(56) References Cited

U.S. PATENT DOCUMENTS

H224 H * 3/1987 Malik et al. .................... 71/92

FOREIGN PATENT DOCUMENTS

| EP | 0 220 902 | * | 5/1987 |
| EP | 0 895 805 | * | 2/1999 |
| WO | 95/03881 | * | 2/1995 |
| WO | 96/20203 | * | 7/1996 |
| WO | 97/17608 | * | 4/1999 |

OTHER PUBLICATIONS

Abstract XP–002164602 of JP 05–043403, Aug. 8, 1991.*

* cited by examiner

Primary Examiner—S. Mark Clardy
(74) Attorney, Agent, or Firm—Linda K. Russell

(57) ABSTRACT

The invention concerns a herbicide composition comprising N-(phosphonomethyl)glycine or one of its salts, at least a compound of formula (I): $RO-(X)_p$ wherein: p represents a decimal number between 1 and 5; X represents the xylose radical; and R represents a linear or branched, saturated or unsaturated alkyl radical comprising 6 to 18 carbon atoms, a dispersing medium both for the active principle and the compound of formula (I), optionally, one or several surfactants and optionally one or several inert adjuvants. The invention also concerns a phytosanitary method using said composition and the use of a product of formula (I), to prepare a herbicide composition.

47 Claims, No Drawings

HERBICIDE COMPOSITION COMPRISING GLYPHOSATE AND AT LEAST A POLYXYLOSIDE ALKYL

The subject of the invention are novel herbicidal compositions containing N-(phosphonomethyl)glycine or one of its salts and one or more alkyl polyxylosides.

A plant protectant enters into a plant either via the leaves (absorption by the leaves) or via the roots (absorption by the roots). Absorption of an active principle by the leaves is difficult and very poor. Aqeuous solutions of plant protectants frequently have low stability over time or are sparingly compatible with the components which are usually present in the end solutions for plant treatment. The herbicides of the N-(phosphonomethyl)glycine family have been on the market for the several years. European Patent Application EP 0 220 902 discloses herbicidal concentrates containing glyphosate and alkyl polyglycosides.

During its studies with the aim of proposing novel formulations of plant protectants which are less harmful to the environment while being as effective as the prior-art formulations, the applicant company has produced the novel concentrate, which is a subject of the present invention.

Subject of the invention is a composition containing
(a) N-(phosophonomethyl)glycine or one of its salts,
(b) at least one compound of the formula (I):

$$RO—(X)_p \qquad (I)$$

in which:
p represents a decimal number between 1 and 5,
X represents the xylose residue, and
R represents a straight-chain or branched, saturated or unsaturated alkyl radical having 6 to 18 carbon atoms,
(c) a dispersing medium for the active principle and compound of the formula (I),
(d) if appropriate one or more other surfactants and
(e) if appropriate one or more inert adjuvants.

Straight-chain or branched, saturated or unsaturated hydrocarbon radical having 6 to 18 carbon atoms is to be understood as meaning, for R, in particular an alkyl radical or an alkenyl radical. R more particularly represents an alkyl radical or an alkenyl radical having 8 to 16 carbon atoms. Examples of the alkyl or alkenyl radical which represents R are those selected from straight-chain or branched hexyl radicals, straight-chain or branched heptyl radicals, straight-chain or branched octyl radicals, straight-chain or branched nonyl radicals, straight-chain or branched decyl radicals, straight-chain or branched decenyl radicals, straight-chain or branched undecyl radicals, straight-chain or branched undecenyl radicals, straight-chain or branched dodecyl radicals, straight-chain or branched tridecyl radicals, straight-chain or branched tetradecyl radicals, straight-chain or branched pentadecyl radicals and straight-chain or branched hexadecyl radicals.

Other examples of branched radicals are those of the formula (II):

$$CH(C_nH_{2n+1})(C_mH_{2m+1})—CH_2—$$

in which m is an integer between 2 and 18, n is an integer between 2 and 18, and the total n+m is greater than or equal to 6, preferably less than or equal to 14.

The oligomeric structure $(X)_p$ can be present in all isomeric forms, whether this is optical isomerism, geometric isomerism or positional isomerism; it can also represent a mixture of isomers.

In formula (I), group R—O— is bound to X by the anomeric carbon of the xylose residue to form an acetal function.

p, which represents the mean degree of polymerization of the saccharide, is more particularly between 1 and 2.5, very particularly between 1 and 2.0.

In a first particular aspect of the present invention, the subject of the invention is a compound of the formula (I) as defined above in which n is less than or equal to 8.

In a second particular aspect of the present invention, the subject of the invention is a compound of the formula (I) as defined above in which m is less than or equal to 6. In this case, R represents more particularly one of the radicals 2-butylhexyl (m=4, n=4), 2-butyldecyl (m=4, n=8) or 2-hexyloctyl (m=6, n=6).

The compounds of the formula (I) as defined above are prepared either by reacting xylose of the formula (III):

$$HO—X \qquad (III)$$

with an excess of alcohol of the formula (IV):

$$ROH \qquad (IV),$$

and eliminating the fatty alcohol of the formula (IV) which has not reacted,
or by reacting xylose of the formula (III) with an alcohol of the formula (V):

$$R—OH \qquad (V)$$

in which $R_1$ has 1 to 4 carbon atoms, more particularly with butanol, to give the acetal of the formula (VI):

$$R_1O—(X)_p \qquad (VI),$$

which acetal of the formula (VI) subsequently undergoes transacetalization by means of an excess of alcohol of the formula (IV) with distillation of the alcohol of the formula (V) formed followed by elimination of the alcohol of the formula (IV) which has not reacted.

In the process as defined hereinabove, the formation reaction of the compound of the formula (I) is carried out in the presence of strong acidic catalysts, such as, for example, mineral acids such as sulphuric acid, hypophosphorous acid or a mixture of these acids.

The alcohol of the formula (IV) which has not reacted is eliminated by methods known to the skilled worker such as, for example, distillation, thin-film distillation, molecular distillation or solvent extraction.

Dispersing medium of the plant protectant and of the compound(s) of the formula (I) is to be understood as meaning, for the purposes of the present invention, any liquid in which the plant protectant and the compound(s) of the formula (I) are soluble or are dispersed. In the case of glyphosate, the dispersing medium is preferably water.

In addition to the compounds of the formula (I) as defined above, the composition can contain other surfactants conventionally used in herbicidal compositions. These surfactants can be anionic, cationic, non-ionic or amphoteric. Examples of such surfactants are described in WO 99/03343, EP 0 508 022, EP 0 531 269, WO 96/22109 or U.S. Pat. No. 4,557,751.

When such surfactants are present in the composition which is a subject of the present invention, they preferably take the form of ethoxylated fatty acid esters described in WO 96/22109, modified vegetable oils described in WO 00/1233 and/or alkoxylated fatty amines described in U.S. Pat No.4,557,751. The contents of the publications WO 96/22109, WO 00/1233 and U.S. Pat. No. 4,557,751 are an integral part of the present description.

When inert adjuvants are present in the composition which is a subject of the present invention, they take the form of, for example, absorbers of ultraviolet rays.

Modified or unmodified vegetable oils which can be mentioned are, more particularly, sunflower oil, linseed oil, soya oil, corn oil, peanut oil, coconut oil, olive oil, palm oil, hydrogenated palm oil or rapeseed oil, either modified or unmodified.

Glyphosphate, or N-(phosphonomethyl)glycine, which is present in the composition can be in free form or in salt form, preferably in the form of a water-soluble salt, such as, for example, monoisopropylamine or trimethylsulphonium salts.

A subject of the invention is a plant-protective treatment method, characterized in that the composition as defined above is used.

The composition is either ready-to-use or in the form of a concentrate which is previously dissolved or dispersed in the water before being sprayed onto the area to be treated, for the preparation of a composition for the plant-protective treatment of plants, in particular in agriculture or for treating ornamental gardens. The dilution rate depends essentially on the minimal effective quantity of the crop protectant required, which is expressed in weight per area to be treated.

As shown in the experimental study described hereinbelow, replacing alkyl polyglucoside compounds by alkyl polyxylosides with the same side chain significantly improves the herbicidal activity of the formulation and thus allows thus the use of less glyphosate per hectare to be treated.

In a last aspect of the present invention, a subject of the invention is the use of a product of the formula (I) as defined above for the preparation of a composition for the plant-protective treatment of plants, in particular in agriculture or for treating ornamental gardens.

Evaluation of the Ability, of the Compounds of the Formula (I), to Stimulate the Herbicidal Activity of Glyphosate Three weeks after sowing, when the plant had reached the 1–2-leaf stage, field experiments on barley were carried out on 8 equally sized plots, and the results were compared with a ninth, untreated, plot of the same size.

Aqueous solutions containing surfactant and glyphosate in the following proportions were applied to each plot at 200 litres per hectare:

|  | Surfactant (in g/litre solution) | Glyphosate (in g/litre solution) |
|---|---|---|
| $S_1$ | $X_1$ : 45 | 90 |
| $S_2$ | $X_1$ : 90 | 180 |
| $S_3$ | $G_1$ : 45 | 90 |
| $S_4$ | $G_1$ : 90 | 180 |
| $S_5$ | $X_2$ : 45 | 90 |
| $S_6$ | $X_2$ : 90 | 180 |
| $S_7$ | $G_2$ : 45 | 90 |
| $S_8$ | $G_2$ : 90 | 180 |

The surfactants combined with glyphosate were the following:

$X_1$: an alkyl polyxyloside mixture of which 45% by weight contain a C8 chain and 55% by weight a C10 chain;

$G_1$: an alkyl polyglucoside mixture of which 45% by weight contain a C8 chain and 55% by weight a C10 chain;

$X_2$: an alkyl polyxyloside mixture containing a branched C11 chain;

$G_2$: an alkyl polyglucoside mixture containing a branched C11 chain;

The experiments were carried out using a randomized design with four replications.

They were scored visually for the first time two months after treatment of the culture.

They were scored for the second time four months after treatment of the culture.

The efficacy relative to the untreated control was scored from 0 to 10. The results are compiled in the following table:

| | Herbicidal efficacy | |
|---|---|---|
| | 2 months after treatment | 4 months after treatment |
| $S_1$ | 8.2 | 9.3 |
| $S_2$ | 9.1 | 9.8 |
| $S_3$ | 7.0 | 8.0 |
| $S_4$ | 8.0 | 8.5 |
| $S_5$ | 8.3 | 9.0 |
| $S_6$ | 9.1 | 9.9 |
| $S_7$ | 7.0 | 7.9 |
| $S_8$ | 8.2 | 8.4 |

The results of this table reveal the positive effective induced by the presence of compounds of the formula (i) in solutions $S_1$, $S_2$, $S_5$ and $S_6$ instead of the alkyl polyglucoside homologues in solutions $S_3$, $S_4$, $S_7$ and $S_8$, respectively, in terms of the herbicidal activity of the active principle.

What is claimed is:

1. Composition containing
   (a) N-(phosophonomethyl)glycine or one of its salts,
   (b) at least one compound of the formula (I):

$$RO-(X)_p \tag{I}$$

in which:
   p represents a decimal number between 1 and 5,
   X represents the xylose residue, and
   R represents a straight-chain or branched, saturated or unsaturated alkyl radical having 6 to 18 carbon atoms,
   (c) a dispersing medium for the active principle and compound of the formula (I).

2. Composition as defined in claim 1, where, in formula (I), R represents an alkyl radical or an alkenyl radical containing 8 to 16 carbon atoms.

3. Composition as defined in claim 2, where, in formula (I), R represents a radical selected from straight-chain or branched hexyl radicals, straight-chain or branched heptyl radicals, straight-chain or branched octyl radicals, straight-chain or branched nonyl radicals, straight-chain or branched decyl radicals, straight-chain or branched decenyl radicals, straight-chain or branched undecyl radicals, straight-chain or branched undecenyl radicals, straight-chain or branched dodecyl radicals, straight-chain or branched tridecyl radicals, straight-chain or branched tetradecyl radicals, straight-chain or branched pentadecyl radicals and straight-chain or branched hexadecyl radicals.

4. Composition as defined in one of claim 1, where, in formula (I), R represents a radical of the formula (II):

$$CH(C_nH_{2n+1})(C_mH_{2m+1})-CH_2- \tag{II}$$

in which m is an integer between 2 and 18, n is an integer between 2 and 18, and the total n+m is greater than or equal to 6.

5. Composition as defined in claim 2, where, in formula (I), R represents a radical of the formula (II):

in which m is an integer between 2 and 18, n is an integer between 2 and 18, and the total n+m is greater than or equal to 6.

6. Composition as defined in claim 3, where, in formula (I), R represents a radical of the formula (II):

in which m is an integer between 2 and 18, n is an integer between 2 and 18, and the total n+m is greater than or equal to 6.

7. Composition as defined in claim 4, where, in formula (II), the total n+m is less than or equal to 14.

8. Composition as defined in claim 5, where, in formula (II), the total n+m is less than or equal to 14.

9. Composition as defined in claim 6, where, in formula (II), the total n+m is less than or equal to 14.

10. Composition as defined in claim 4, where, in formula (II), n is less than or equal to 8.

11. Composition as defined in claim 5, where, in formula (II), n is less than or equal to 8.

12. Composition as defined in claim 8, where, in formula (II), n is less than or equal to 8.

13. Composition as defined in claim 7, where, in formula (II), n is less than or equal to 8.

14. Composition as defined in claim 8, where, in formula (II), n is less than or equal to 8.

15. Composition as defined in claim 9, where, in formula (II), n is less than or equal to 8.

16. Composition as defined in claim 4, where, in formula (II), m is less than or equal to 6.

17. Composition as defined in claim 5, where, in formula (II), m is less than or equal to 6.

18. Composition as defined in claim 7, where, in formula (II), m is less than or equal to 6.

19. Composition as defined in claim 9, where, in formula (II), m is less than or equal to 6.

20. Composition as defined in claim 11, where, in formula (II), m is less than or equal to 6.

21. Composition as defined in claim 13, where, in formula (II), m is less than or equal to 6.

22. Composition as defined in claim 15, where, in formula (II), m is less than or equal to 6.

23. Composition as defined in claim 17, where, in formula (II), m is less than or equal to 6.

24. Composition as defined in claim 19, where, in formula (II), m is less than or equal to 6.

25. Composition as defined in claim 16, where, in formula (I), R represents one of the radicals 2-butylhexyl (m=4, n=4), 2-butyldecyl (m=4, n=8) or 2-hexyloctyl (m=6, n=6).

26. Composition as defined in claim 18, where, in formula (I), R represents one of the radicals 2-butylhexyl (m=4, n=4), 2-butyldecyl (m=4, n=8) or 2-hexyloctyl (m=6, n=6).

27. Composition as defined in claim 20, where, in formula (I), R represents one of the radicals 2-butylhexyl (m=4, n=4), 2-butyldecyl (m=4, n=8) or 2-hexyloctyl (m=6, n=6).

28. Composition as defined in claim 22, where, in formula (I), R represents one of the radicals 2-butylhexyl (m=4, n=4), 2-butyldecyl (m=4, n=8) or 2-hexyloctyl (m=6, n=6).

29. Composition as defined in claim 24, where, in formula (I), R represents one of the radicals 2-butylhexyl (m=4, n=4), 2-butyldecyl (m=4, n=8) or 2-hexyloctyl (m=6, n=6).

30. Composition as defined in claim 1, where the dispersing medium is water.

31. Composition as defined in claim 2, containing, in addition to compounds of the formula (I) as defined above, one or more surfactants selected from anionic, cationic, nonionic or amphoteric surfactants.

32. Composition as defined in claim 3, containing, in addition to compounds of the formula (I) as defined above, one or more surfactants selected from anionic, cationic, nonionic or amphoteric surfactants.

33. Composition as defined in claim 5, containing, in addition to compounds of the formula (I) as defined above, one or more surfactants selected from anionic, cationic, nonionic or amphoteric surfactants.

34. Composition as defined in claim 1, containing, in addition to compounds of the formula (I) as defined above, one or more surfactants selected from the ethoxylated fatty acid esters, modified vegetable oils and alkoxylated fatty amines.

35. Composition as defined in claim 2, containing, in addition to compounds of the formula (I) as defined above, one or more surfactants selected from the ethoxylated fatty acid esters, modified vegetable oils and alkoxylated fatty amines.

36. Composition as defined in claim 3, containing, in addition to compounds of the formula (I) as defined above, one or more surfactants selected from the ethoxylated fatty acid esters, modified vegetable oils and alkoxylated fatty amines.

37. Composition as defined in claim 1, additionally containing one or more inert adjuvants.

38. Composition as defined in claim 1, in which glyphosate, or N-(phosphonomethyl)glycine, is in the form of a water-soluble salt.

39. Composition as defined in claim 1, in which glyphosate, or N-(phosphonomethyl)glycine, is in the form of a water-soluble salt.

40. Composition as defined in claim 39, wherein said water-soluble salt is monoisopropylamine salt or trimethylsulphonium salt.

41. Composition as defined in claim 39, wherein said water-soluble salt is monoisopropylamine salt or trimethylsulphonium salt.

42. Method of plant treatment, comprising treating plants with the composition of claim 1.

43. Method of plant treatment, comprising treating plants with the composition of claim 10.

44. Method of plant treatment, comprising treating plants with the composition of claim 20.

45. Method of plant treatment, comprising treating plants with the composition of claim 30.

46. Method of plant treatment as in claim 45, comprising plants which are agricultural in nature.

47. Method of plant treatment as in claim 45, comprising plants which are ornamental in nature.

* * * * *

UNITED STATES PATENT AND TRADEMARK OFFICE
CERTIFICATE OF CORRECTION

PATENT NO.    : 6,670,306 B2
DATED         : December 30, 2003
INVENTOR(S)   : Alain Milius and Bernard Brancq It is certified that error appears in the above-identified patent and that said Letters Patent is hereby corrected as shown below:

Column 5,
Line 26, please replace "Claim 8" with -- Claim 6 --.

Signed and Sealed this

Twenty-sixth Day of October, 2004

JON W. DUDAS
*Director of the United States Patent and Trademark Office*